US006479273B1

(12) United States Patent
Bogedain et al.

(10) Patent No.: US 6,479,273 B1
(45) Date of Patent: Nov. 12, 2002

(54) FILTRATION METHOD FOR SEPARATING VIRUSES

(75) Inventors: Christoph Bogedain, Munich (DE); Gerhard Maass, Sindelsdorf (DE); Markus Hörer, Martinsried (DE)

(73) Assignee: MediGene Aktiengesellschaft (DE)

( * ) Notice: Subject to any disclaimer, the term of this patent is extended or adjusted under 35 U.S.C. 154(b) by 0 days.

(21) Appl. No.: 09/380,366

(22) PCT Filed: Mar. 5, 1998

(86) PCT No.: PCT/EP98/01257

§ 371 (c)(1), (2), (4) Date: Dec. 22, 1999

(87) PCT Pub. No.: WO98/39420

PCT Pub. Date: Sep. 11, 1998

(30) Foreign Application Priority Data

Mar. 6, 1997 (DE) .......................................... 197 09 186

(51) Int. Cl.$^7$ ................................................. C12N 7/02
(52) U.S. Cl. .................................... 435/239; 435/320.1
(58) Field of Search .............................. 435/239, 320.1, 435/235.1

(56) References Cited

FOREIGN PATENT DOCUMENTS

| CA | 2169122 | | 2/1996 | | |
|---|---|---|---|---|---|
| DE | 1951800 | * | 4/1971 | .......... | A61K/23/00 |
| WO | 97/08298 | * | 3/1997 | ............ | C12N/7/02 |

OTHER PUBLICATIONS

Conway et al (Journal of Virology 71(11):8780–8789, Nov. 1997.*
Chiorini et al., "High–Efficiency Transfer of the T Cell Co–Stimulatory Molecule B7–2 to Lymphoid Cells Using High–Titer Recombinant Adeno–Associated Virus Vectors," *Human Gene Therapy* 6:1531–1541 (1995).
Kotin, "Prospects for the Use of Adeno–Associated Virus as a Vector for Human Gene Therapy," *Human Gene Therapy* 5:793–801 (1994).
Annual Conference of the Virology Society. Abstract No. P54 (1996), and English translation.
Whartenby et al., "Gene–Modified Cells for the Treatment of Cancer," *Pharmac. Ther.* 66:175–190 (1995).
Gröner et al., Abstract, "Eliminierung von Viren durch nm–Filtration aus Proteinlösungen," Frühjahrstagung der Gesellschaft für Virologie, P 300, (1995) and concise explanation.
Eibl et al., "Nanofiltration of Immunoglobulin with 35–nm Filters Fails to Remove Substantial Amount of HCV," Biologicals 24:285–287 (1996).
Römisch et al., "Erhöhte Kapazität zur Eliminierung von Viren," Krankenhauspharmazie Nr. 12:504–507 (1995).
PLANOVA, BMM Process Filter, Validatable Virus Removal Filters, ASAHI Chemical Industry Co., Ltd., Tokyo, Japan, (Jan. 1996).
Roberts, "Efficient Removal of Viruses by Novel Polyvinylidene Fluoride Membrane Filter," J. Virological Methods 65:27–31 (1997).
Maerz et al., "Improved Removal of Viruslike Particles from Purified Monoclonal Antibody IgM Preparation Via Virus Filtration," Nature Biotechnology 14:651–652 (1996).
Manabe, Abstract, "Removal of Virus Through Novel Membrane Filtration Method," Dev. Biol. Stand. 88:81–90 (1996).
O'Grady et al., Abstract, "Virus Removal Studies Using Nanofiltration Membranes," Dev. Biol. Stand. 88:319–326 (1996).
Burnouf–Radosevich et al., Abstract, "Nanofiltration, a New Specific Virus Elimination Method Applied to High–Purity Factor IX and Factor XI Concentrates," Vox Sang 67(2):132–138 (1994).
Römisch et al., "Erhöhte Kapazität zur Eliminierung von Viren," Krankenhauspharmazle Nr. 12:404–407 (1995).
DiLeo et al., "Size Exclusion Removal of Model Mammalian Viruses Using a Unique Membrane System, Part 1: Membrane Qualification," Biologicals 21:275–286 (1993).
PLANOVA, BMM Process Filter, "A Validatable Process Filter for the Effective Removal of Viruses," ASAHI Chemical Industry Co., Ltd., Tokyo, Japan (1994).
Animal Cell Technology: Basic & Applied Aspects, Ed.: Murakami et al. (1992), Kluwer Academic Publishers, Proceedings of the Fourth Annual Meeting of the Japanese Association for a Animal Cell Technology, Fukuoka, Japan, Nov. 13–15, 1991, "Virus Removal and Inactivation in Process Validation," p. 15–30.
Ullmann's Encyclopedia of Industrial Chemistry, vol. B8, "Environmental Protection and Industrial Safety II," Ed.: Weise (1995), p. 9.
Third International Symposium on HCV, Sep. 16–17, 1991, Strasbourg, France, "Program and Abstracts," V39, Muchmore et al., "Hepatitis C Virus Particle Size as Determined by Bemberg Microporous Membrane (BMM) Removal of Infectivity, Confirmed by Chimpanzee Inoculation Tests".
Troccoli et al., Abstract, "Removal of Viruses from Human Intravenous Immune Globulin by 35 nm Nanofiltration," Biologicals Dec;26(4):321–9 (1998).

* cited by examiner

*Primary Examiner*—Mary E. Mosher
(74) *Attorney, Agent, or Firm*—Clark & Elbing LLP

(57) ABSTRACT

The invention relates to a process for separating viruses of different sizes, with the virus-containing solution preferably being filtered through one or more filter membranes.

38 Claims, No Drawings

FILTRATION METHOD FOR SEPARATING VIRUSES

This application claims priority from International Application PCT/EP98/01257,filed Mar. 5, 1998 and German Patent Application DE 197 09 186.5, filed Mar. 6, 1997.

The invention relates to a process for separating viruses of different sizes, with the virus-containing solution preferably being filtered through one or more filter membranes.

The original aim of gene therapy was to cure genetic diseases by altering body cells genetically in a suitable manner. Nowadays, the term gene therapy is extended to include genetically altered cells which can also be employed therapeutically for curing diseases which do not: have a genetic origin, such as viral diseases, for example.

The genetic alteration of therapeutically active cells requires suitable methods for transferring the nucleic acid, i.e. DNA or RNA, which brings about the genetic alteration of the cell. The nucleic acids which are to be transferred are frequently also described as being so-called transgenes, even when they do not exercise the functions of a gene, e.g. when they are anti-sense nucleic acids. In addition to the direct gene transfer of so-called naked nucleic acids, genetically altered viruses have also proved to be suitable for effecting the gene transfer. At present, retroviruses, adenoviruses or adeno-associated viruses (AAVs), inter alia, are being genetically altered so that they can each be used as a carrier (viral vector) of the transgene(s) for the gene transfer. An important consideration when developing suitable viral vectors is that of the safety aspects when using these vectors in gene therapy. In general, therefore, replication-deficient viruses are developed, that is viruses which, while being able to infect a cell and transfer the transgene(s) into the cell, are unable themselves to replicate in this cell. This is achieved, for example, by deleting the genes which are important for virus replication, for example the genes encoding structural proteins, and, where appropriate, incorporating the transgene(s) in place of them. The preparation of relatively large quantities, which are suitable for the use in gene therapy, of replication-incompetent viruses requires so-called helper viruses, which compensate, in the cell, for the defect in a replication-incompetent virus. The following examples of retroviral vectors and adeno-associated vectors are intended to clarify the general principle:

Replication-deficient retroviral vectors are derived from wild-type retroviruses, which constitute a separate family of eucaryotic viruses whose genetic material (structural genes and regulatory genes) is composed of single-stranded RNA. The viruses are composed of spherical, enveloped virus particles having a diameter of approx. 80–120 nm and an inner capsid, which contains two copies of the genomic RNA in the form of a ribonucleo-protein. For preparing retroviral vectors, one or more structural genes (gag, pol and/or env) is/are replaced by the transgene(s). The LTR (long terminal repeat) regions which are still present at the 5' and 3' ends contain, as cis-active elements, regulatory sequences such as a promotor, polyadenylation signals and the sequences which are required for integration into the genome. It is possible, therefore, for the retroviral vector only to contain the LTR regions which flank the transgene(s) The replication of a replication-deficient retroviral vector therefore requires, for example, a helper virus which contains one or more of the abovementioned retroviral structural genes and thus complements the deleted structural gene(s) (Whartenby, K. A. et al. (1995) Pharmac. Ther., 66, 175–190).

Replication-deficient adeno-associated viral vectors are derived from the wild-type AAV, which is a non-autonomously replicating representative of the parvoviruses and constitutes a single-stranded DNA virus having a diameter of approx. 25 nm. Today, it is possible to differentiate between the serologically distinguishable types AAV-1, AAV-2, AAV-3, AAV-4 and AAV-5. AAV viruses can either integrate into the genome of the host cell or replicate in the host cells in the presence of a helper virus. Adenoviruses were first of all found as possible helper viruses. In vertebrates, for example, adenoviruses form a group of more than 80 serologically distinguishable serotypes and contain an outer, icosahedral protein coat (capsid) and an inner, central DNA-protein body (core). The capsid is in turn composed of 252 subunits, so-called capsomers. In general, the adenoviruses have a diameter of approx. 70–90 nm and contain, as the genetic material a double-stranded, linear DNA at the 5' and 3' ends of which there are ITR regions (inverted terminal repeats). AAV replication (lyric phase) now requires, in particular, the expression of early adenoviral genes such as, e.g., the E1a, E1b, E2a and E4 genes and the VA RNA (Kotin, R. M. (1994) Human Gene Therapy, 5, 793–801). However, other helper viruses, such as the herpesviruses, which is a group of double-stranded DNA viruses which are pathogenic to humans and animals and which have a diameter of approx. 120–200 nm, with the capsid having an icosahedral structure and being composed of 162 capsomers, are also suitable. The herpesviruses can be divided into three subfamilies, with, for example, type I and type 2 herpes simplex viruses (HSV) belonging to the Alphaherpesvirinae, cytomegalovirus (CMV), for example, belonging to the Betaherpesvirinae, and Epstein Barr virus (EBV), for example, belonging to the Gammaherpesvirinae.

In analogy with the retroviral vectors, one or more of the rep genes which are required for replication (e.g. rep 40, rep 52, rep 68 and/or rep 78) or the cap genes which are required for the capsid structure (e.g. VP-1, VP-2 and/or VP-3) can, for example, be replaced with the transgene(s) when preparing adeno-associated vectors. The ITR regions which are still present at the 5' and 3' ends are needed, as cis-active elements, for packaging the transgene into infectious, recombinant AAV particles and for the replication of the DNA of the recombinant AAV genome (Kotin, R. M. (1994), loc. sit.).

Cotransfection of a eucaryotic cell with two recombinant AAV plasmids and a helper virus (Chiorini, J. A. et al. (1995) Human Gene Therapy, 6, 1531–1541) is an advantageous method for preparing relatively large quantities of recombinant AAV particles. The first recombinant AAV vector contains the transgene(s) which is/are flanked by the two ITR regions. The second recombinant AAV plasmid contains the AAV genes which are required for preparing the particles (rep and cap genes). The absence of functional ITR regions in the second vector prevents the rep and cap genes being packaged into AAV particles and undesirable wild-type AAV thus being formed. Mammalian cells, for example COS-7 cells, which are permissive both for the recombinant AAV vectors and for the helper virus, for example adenovirus, i.e. which provide the prerequisites for infection and replication, are then transfected with the two recombinant AAV vectors and the helper virus. The adenovirus is particularly suitable for use as the helper virus since it can infect a broad spectrum of target cells and can replicate in the cells themselves. When the transfected cells are cultured, the AAV non-structural protein genes and the AAV structural protein genes are expressed, the transgene DNA is replicated and the recombinant AAV particles (rAAV particles) are packaged and assembled. The rAAV particles contain the transgene(s), which is/are flanked at both ends by the ITR regions, in the form of single-stranded DNA. At the same time, the helper virus replicates in these cells, something which generally ends, when adenoviruses are used as helper viruses, in the lysis and death of the infected cells after a few days. The resulting viruses (adenoviruses and rAAV particles) are either in part released into the cell culture supernatant or else remain in the lysed cells. For this reason, the cells are generally disrupted using cell disruption methods which are known to the skilled person, such as alternately freezing and thawing or by means of enzymic hydrolysis, for example with trypsin (Chiorini, J. A. et al. (1995), loc. sit.), in order to achieve essentially complete release of the viruses.

A significant disadvantage associated with preparing viral vectors using helper viruses is the formation of a mixed population of recombinant virus particles and helper viruses, which population has to be subjected to further purification. In particular, contaminations with adenovirus should be avoided or minimized when using viral vectors in gene therapy because of the potential pathogenicity.

The customary methods for depleting or eliminating adenoviruses, for example, in mixed populations containing AAV particles, for example, are density gradient centrifugation or heat inactivation, or a combination of the two methods. The mode of action of density gradient centrifugation is based, in this case, on a minor difference in the density of the adenoviruses (1.35 g/cm$^3$) and the AAV particles (1.41 g/cm$^3$) which can be exploited, for example, in CsCl density gradient centrifugation. Because of the small difference in the density of the viruses and the fact that the quantity of the adenoviruses is from approx. 10 to 100 times higher than that of the AAV particles, the regions in which the AAV particles and the adenoviruses are located after the CsCl density gradient centrifugation are very close to each other such that it is not possible to separate the two viruses quantitatively by carrying out one or more density gradients. Furthermore, the mixed population has to be present in a relatively small volume, since density gradient centrifugation can only be carried out using relatively low volumes. Routine use on an industrial scale is not therefore technically or financially feasible. In addition, it is not possible to separate the adenoviruses quantitatively from the mixed population.

The mode of action of heat inactivation is based on the adenoviruses and the AAV particles, for example, having different thermal stabilities. Heating a mixed population of adenoviruses and AAV particles to 56–65° C. leads to more or less selective heat inactivation of the adenoviruses with there only being a slight loss in the activity of the AAV particles. However, the disadvantage of this method is that, when the preparation is used in gene therapy, the denatured adenovirus proteins which are still present are able to evoke a powerful cellular immune response in the patient (Smith, C. A. et al. (1996) J. Virol., 70, 6733–6740).

It is also known that filter membranes having a pore size which ensures that particles in the nanometer range are removed can be employed for separating off viral contaminants from pharmaceutical products which have to be virus-free (Scheiblauer, H. et al. (1996), Jahrestagung der Gesellschaft fur Virologie [Annual Conference of the Virology Society], Abstract No. P54). While Scheiblauer et al. (1996, loc. sit.) point out that the viruses are retained on the basis of their size, it was not reported that the different viruses were separated quantitatively.

The object of the present invention is therefore to provide a process in which different viruses present in a mixed population can be separated from each other and which can be used even in the case of relatively large volumes.

It has now been found, surprisingly, that a separation, which is essentially quantitative or is adequate for use in gene therapy, of viruses of different sizes is achieved, in a manner which is both simple and applicable on an industrial scale, by subjecting a virus-containing solution to one or more filtrations.

One part of the subject matter of the present invention is therefore a process for separating viruses of different sizes, with a virus-containing solution preferably being filtered through one or more filter membranes.

Advantageously, the filter membranes are composed of polyvinylidene fluoride, polytetrafluoromethylene, polypropylene, modified or unmodified polyether sulfone, cellulose acetate, cellulose nitrate, polyamide or regenerated cellulose, for example cuprammonium-regenerated cellulose, preferably of polyvinylidene fluoride. Examples of such membranes having a pore size which permits the removal of particles having a size of approx. 40–400 nm are the Ultipor membranes from Pall GmbH, 63303 Dreieich, which have pore sizes of approx 50 nm or approx. 100 nm, the Asahi Chemical's Bemberg microporous membranes from Asahi Chemical Industry Ltd., Tokyo, Japan, which have pore sizes of approx. 15 nm, approx. 35 nm or approx. 72 nm, or corresponding membranes from Sartorius AG, 37075 Gottingen or Schleicher and Schuell GmbH, 37582 Dassel. In general, the filter membranes in accordance with the present invention have a pore size which permits the removal of particles of up to approx. 120 nm, in particular of up to approx. 60 nm, especially of up to approx. 50 nm, preferably from approx. 25 to 60 nm. The choice of a filter having a suitable pore size depends, first and foremost, on the sizes of the viruses to be separated, which viruses generally have a diameter of up to approx. 250 nm, preferably up to approx. 120 nm, in particular up to approx. 60 nm. An additional selection criterion when choosing a filter having a suitable pore size is the difference in the sizes of the viruses to be separated, which difference should in general amount to at least approx. 5 nm, preferably at least approx. 10 nm, in particular at least approx. 20 nm, especially at least approx. 30 nm and, most preferably, approx. 40 nm. Using the sizes of the viruses to be separated, and the difference in sizes resulting from this, as a basis, the skilled person can then select a filter which has a pore size which is suitable for separating the viruses which are to be separated. The efficacy of the selected filter(s) can then be readily tested routinely by means of simple filtration experiments.

Thus, a filter having a pore size which enables the titer of viruses having a diameter of more than approx. 50 nm to be reduced, preferably the Pall-Ultipor VF DV50 membrane or the Asahi-Planova 35 membrane, which have already been mentioned above, is suitable, in a particularly advantageous manner, for separating rAAV particles and adenoviruses. In particular, these filters make it possible not only to achieve an essentially quantitative removal of infectious adenoviruses from the mixed population but also to achieve a high yield, of approx. 70–90%, of rAAV particles.

Within the meaning of the present invention, the terms "pore size", "removal rate", "effective size" or "pore size which permits particles having a particular minimum size to be removed", which are used by different filter manufacturers, are equivalent terms.

Within the meaning of the present invention, the term virus or viruses encompasses not only naturally occurring viruses or viruses which have been altered by genetic manipulation, i.e. so-called recombinant viruses, but also virus particles, i.e. both infectious and non-infectious viruses, virus-like particles ("VLP"), such as papillomavirus-like particles in accordance with WO 96/11272, and capsids which contain nucleic acids, but can also be empty, and parts thereof, in particular, one or more, preferably several subunits or capsomers, especially when several capsomers are associated or combined such that they constitute at least approx. 50%, preferably at least 80%, especially approx. 90%, of the capsid. The viruses have, in particular, an essentially spherical shape, in particular possessing icosahedral symmetry.

According to the present invention, the viruses can be classified, in accordance with their size, into the following three groups:

The first group represents viruses which have a diameter of up to approx. 60 nm and which are generally derived, for example, from Flaviviridae having a diameter of approx. 40–60 nm, such as, for example, flavivirus or hepatitis C virus (HCV), from papillomaviruses having a diameter of approx. 55 nm, such as human papillomaviruses 16 or 18 (HPV 16 and HPV 18), from papovaviruses having a diameter of approx. 45 nm, such as polyomavirus, from hepadnaviruses having a diameter of approx. 22–42 nm, such as hepatitis B virus (HBV), from picornaviruses having a diameter of approx. 22–30 nm, such as hepatitis A virus (HAV) or poliovirus, or from parvoviruses having a diameter of approx. 18–26 nm, such as adeno-associated virus (AAV) or rAAV particles having a diameter of approx. 25 nm.

The second group represents viruses which have a diameter of from approx. 60 nm up to approx. 120 nm and which are generally derived, for example, from influenza viruses having a diameter of approx. 80–120 nm, from retroviruses having a diameter of approx. 80–120 nm, such as oncoviruses, lentiviruses, such as HIV-1 or HIV-2, spuma-viruses or HTLV viruses, from adenoviruses having a diameter of approx. 65–90 nm, from reoviruses having a diameter of approx. 60–80 nm, such as coltivirus or rotavirus, or from togaviruses having a diameter of approx. 60–70 nm.

The third group represents viruses which have a diameter of from approx. 120 nm up to approx. 250 nm and which are generally derived, for example, from paramyxoviruses having a diameter of approx. 150–250 nm, or from herpesviruses having a diameter of approx. 120–200 nm, such as HSV-1 or HSV-2, CMV or EBV.

According to the present invention, the viruses of one of the abovementioned groups can particularly advantageously be separated from viruses of the other groups. However, different viruses which belong to one and the same group, out of the abovementioned groups, can also be separated from each other provided there is a sufficient difference in their sizes, preferably as already described in detail above. In particular, the viruses of the first group can be separated from the viruses of the second and/or the third group; especially, AAV particles can particularly advantageously be separated from adenoviruses and/or herpesviruses.

For example, the process according to the invention makes it possible, in a particularly advantageous manner, to remove adenoviruses, both in the case of material which has been prepurified, for example by means of one or more density gradients, and in the case of unpurified material, from the supernatants of an rAAV culture, for example, with the adenoviruses remaining in the retentate and the rAAV particles being present in the filtrate. Advantageously, a prefiltration, as described in more detail below, is carried out prior to the actual separation of the desired viruses.

Another preferred embodiment of the process according to the invention therefore extends to a prepurification of the virus-containing solution, for example by means of one or more density gradients and/or by means of one or more prefiltrations. Particular preference is given to a prepurification using one or more membrane filters which allow the viruses which are to be separated to pass but which nevertheless retain larger impurities. In general, the prepurification prevents, or renders more difficult, the clogging of the filter, which brings about the subsequent separation of the desired viruses, by constituents of the virus culture which are not removed, or are not adequately removed, even by centrifugation at low speed. In this connection, the membrane filter for prepurifying viruses of the abovementioned first group, for example, has a pore size of at least approx. 60 nm, while the membrane filter for prepurifying viruses of the first and/or second group has a pore size of at least approx. 120 nm and a membrane filter for prepurifying viruses of the first, second and/or third group has a pore size of at least approx. 250 nm. For example, a membrane filter having a pore size of approx. 100 nm, such as the Ultipor $N_{66}$ filter (Pall GmbH, 63303 Dreieich), is particularly well suited for prepurifying a mixed population of rAAV particles and adenoviruses.

In another preferred embodiment, the pH of the virus-containing solution is adjusted with suitable buffers, for example tris.Cl buffers (tris(hydroxymethyl)aminomethane), to approx. 6–10, preferably to approx. 7.0–8.5, in particular to approx. 8.0, thereby making it possible, for example, to increase the yields, preferably the yields of AAV. It is also particularly preferred if the virus-containing solution additionally contains protein or polypeptide, for example in the form of fetal calf serum (FCS) or serum albumin, in connection with which the nature or origin of the protein is not important. In general, the proportion of the protein, for example in the form of FCS, is not more than approx. 30% (v/v), preferably approx. 15% (v/v), in particular approx. 10% (v/v).

In another preferred embodiment of the process according to the invention, at least approx. 1–10 ml, preferably approx. 2–5 ml, in particular approx. 3 ml, of the virus-containing solution is/are filtered per approx. 1 $cm^2$ of filter surface, especially not more than approx. 2–2.5 ml of solution per approx. 1 $cm^2$ of filter surface. In general, this achieves a high yield of rAAV particles, for example, while at the same time achieving the removal of the adenoviruses, for example. Particular preference is given to separating off cell constituents in the virus culture, prior to the actual separation, by means of centrifuging at low speed, for example at up to approx. 1000 times gravitational acceleration (1000 g), preferably at up to approx. 500 g, in particular at up to approx. 300 g. In connection with this, it is advantageous to subsequently carry out a prefiltration as already described in more detail above. In this way, it was possible, for example, after separating off the cell constituents at approx. 300 g and prefiltering the mixed population through a membrane filter having a pore size of approx. 100 nm, to determine the capacity of a filter having a pore size of approx. 50 nm to be 2 ml/$cm^2$ of filter surface. Within the meaning of the present invention, capacity is understood as being the volume which, per unit area of filter surface, ensures a high is yield of the desired viruses.

The advantages of the process according to the invention are, in particular, a separation, which is simple and inexpensive and therefore also applicable on an industrial scale, of viruses of different sizes under particularly mild conditions, with the separation resulting, in a particularly advantageous manner, in a high yield of purified viruses. A further advantage of the present invention is that the viruses which have been purified in accordance with the invention can, for example, be employed directly as viral vectors for gene therapy since they are adequately free of other viruses, for example pathogenic viruses. Thus, it was not possible, for example, to detect any adenoviruses in an rAAV-containing solution, which had been purified in accordance with the process according to the invention, using a replication test in which the development of a cytopathic effect in permissive cells within a period of, for example, 14 days after coincubating with a corresponding solution would indicate the presence of infectious adenoviruses. Furthermore, use of the PCR reaction and DNA hybridization demonstrated that adenoviral nucleic acids were reduced by a factor of at least approx. $3 \times 10^3$, preferably approx. $10^3$–$10^4$-fold. However, the small residual fraction of adenoviral DNA which remains in the filtrate is not associated with replication-competent adenoviruses and is consequently harmless. The decrease in adenoviral constituents, for example free adenovirus proteins and subviral particles, was particularly surprising since these constituents are perfectly capable of inducing a nonspecific immune response when the viral vectors are used in gene therapy in a patient and could consequently cast doubt on the therapy. In the case of adenoviruses, for example, the reduction in the titer, i.e. the factor by which the titer of the viruses to be removed was decreased, was, in accordance with the process according to the invention, more than 9 logs, i.e. after a mixed population of rAAV particles and $10^9$ adenoviruses had been filtered in accordance with the invention, no adenovirus was then detected in the filtrate.

The following examples are intended to clarify the invention without limiting it thereto:

EXAMPLES

Example 1

Filtration of a Mixed Population of rAAV Particles and Adenoviruses 1.1 A mixed population of rAAV type 2 particles, which contain the gene encoding T cell-costimulating protein B7-2 as the transgene, and wild-type adenovirus type 5 was prepared in accordance with the method of Chiorini, J. A. et al. (1995, loc. sit.), with the cells, which are already exhibiting a marked cytopathic effect, together with the supernatant, being harvested 3 days after infection with the adenoviruses. The cells, together with the supernatant, were then disrupted by being frozen and thawed three times. Insoluble cell constituents were removed by a 10-minute centrifugation at 300 g. The content of fetal calf serum (FCS) was then adjusted to 10% and tris.Cl buffer (pH 8.0) was added to the preparation to give a final concentration of 100 mM. The preparation, from which insoluble cell constituents had been removed and which had been adjusted, was supplied, at 2.5 bar, to a filter system which contained a Pall-Ultipor $N_{66}$ membrane (from Pall GmbH, 63303 Dreieich) having a pore size of 0.1 μm, as the prefilter, and also a Pall-Ultipor VF DV50 membrane, for separating the two viruses. In this way, not more than 2 ml of the preparation were filtered per 1 $cm^2$ of filter surface.

1.2 The starting material was the cell culture supernatant of rAAV particles in accordance with the protocol elaborated by Chiorini, J. A. et al. (1995, loc. sit.). Three to four days after infecting the cells with the adenovirus, the cells, together with the supernatant, were combined. Tris.Cl buffer (pH 8.0) was added to the preparation to give a final concentration of 30 mM. The suspension was frozen and thawed three times in order to disrupt the cells. The step of concentrating the viruses by means of a CsCl density gradient concentration was carried out after the filtration.

The preparation was supplied to a filter system which comprises a prefilter and a Planova 35 hollow fiber filtration element having a pore size of 35 nm. The pressure of 1.5 bar was applied to the prefilter and a pressure of 0.5 bar was applied to the Planova 35 filter. The quantity of the filtered volume was at most 2.5 ml per $cm^2$ of filter surface in the case of the prefilter and at most 7 ml per $cm^2$ of filter surface in the case of the Planova 35 filter.

Example 2

Replication Test

I. A part of an rAAV preparation was filtered, as in example 1, using a filter system which had a 5 $cm^2$ filter surface. The filtrates were collected in several aliquots of 1.5 ml. A control aliquot remained unfiltered. In each case, seven 1:10 dilution steps were prepared from the filtered aliquots and from the unfiltered control. For the replication test, HeLa cells were grown, as a confluent cell layer, in 48-well plates. The supernatant was withdrawn from the wells down to a residual volume of 100 μl. In each case, 100 μl of the dilution series prepared from each of the filtered aliquots and from the unfiltered control were in each case transferred to one well. After the viruses had adsorbed to the cells for 3 h, 500 μl of complete medium were added. Over a period of a week, daily monitoring was carried out in order to check whether a cytopathic effect (CPE) was visible. If required, the medium was changed. The CPE would be brought about by the viruses replicating in the HeLa cells. Replication ultimately ends in the death of the infected cell and in the release of the progeny viruses.

Table 1 shows a typical result. Whereas a CPE was detectable, in the case of the unfiltered control, up to the 4th dilution step, the cell layer was intact after 7 days in the case of all the filtered aliquots which were investigated. This signifies that the titer of infectious adenoviruses in the unfiltered material was of the order of size of $10^5$/ml whereas there was no longer any infectious adenovirus in the filtered material. A comparable titer was detectable in the retentate, that is in the material which was present directly above the membrane and which had collected there.

TABLE 1

Development of a cytopathic effect 7 days after coincubating HeLa cells with filtered and unfiltered packaging supernatants

| Sample | Experiment | Dilution step | | | | | | | |
|---|---|---|---|---|---|---|---|---|---|
| | | 0 | $10^{-1}$ | $10^{-2}$ | $10^{-3}$ | $10^{-4}$ | $10^{-5}$ | $10^{-6}$ | $10^{-7}$ |
| Control | 1 | + | + | + | + | + | − | − | − |
| | 2 | + | + | + | + | + | − | − | − |
| Aliquot 1 | 1 | − | − | − | − | − | − | − | − |
| | 2 | − | − | − | − | − | − | − | − |
| Aliquot 2 | 1 | − | − | − | − | − | − | − | − |
| | 2 | − | − | − | − | − | − | − | − |
| Aliquot 3 | 1 | − | − | − | − | − | − | − | − |
| | 2 | − | − | − | − | − | − | − | − |
| Retentate | 1 | + | + | + | + | + | − | − | − |
| | 2 | + | + | + | + | + | − | − | − |

II. The adenovirus titer of an adenovirus preparation which had been concentrated by means of a cesium chloride density gradient centrifugation was determined as described above. According to this titer determination, $10^8$ adenoviruses were taken up, per ml, in MEM medium containing 10% FCS and 50 mM tris.Cl (pH 8.0). 10 ml of this adenovirus suspension were treated with a filter system as described in Example 1, i.e. a total of $10^9$ infectious adenoviruses were applied. The resulting 10 ml of filtrate were applied to a 175 cm² culture surface area containing 80% confluent HeLa cells. The flask was incubated for 5 days. After this period, no CPE was visible. Since the cells were then confluent and a longer experimental period was desired, the cells were split 1:5. The five resulting HeLa cultures were then observed over a further period of 5 days. Still no CPE was visible. This indicated that there was a complete absence of infectious adenoviruses in the filtrate.

Example 3
Detection of Adenoviral Nucleic Acids
a) RT-PCR Reaction

Part of an rAAV preparation was filtered as described in Example 1; one part remained unfiltered to act as the control. In each case, $3 \times 10^6$ cells from the melanoma cell line M3HK were grown in a 75 cm² cell culture flask. Four such flasks were prepared and exposed to 50 Gy of irradiation with X-rays. The X-rays had a very strong effect in promoting the rAAV-mediated expression of the foreign gene. The medium was in each case drawn off and 1.5 ml of complete medium without serum were added to each flask. In addition, 0.5 ml of the unfiltered control supernatant was then added to one of the flasks, with 0.5 ml from each of two filtered aliquots being added to two of the flasks, and medium being added to one flask as the negative control. After 3 days of incubation at 37° C. and 10% $CO_2$, RNA was prepared from the cell material in each flask (Chomchinski, P. and Sacchi, N., Anal. Biochem. 162, 156–159, 1987) The RNA preparation was subjected to a semiquantitative RT-PCR reaction. The primer pairs described by Cotten and coworkers (Cotten, M., Virology, 205, 254–261, 1994) were used for detecting adenoviral transcripts and the ubiquitous β-actin transcript.

Whereas it was possible to detect the adenoviral E1A transcript in four out of 5 dilution steps in the case of the unfiltered control, it was not possible to detect this transcript in the dilution steps using the filtered aliquots or in the negative control. By contrast, β-actin transcripts were detectable in all the samples treated in parallel. b) DNA Hybridization The starting material was a filtered rAAV preparation as described in Example 1 as well as a portion of this preparation which had been left unfiltered and which acted as the control. Tris.Cl (pH 7.8) was added to the filtered aliquots and to the unfiltered control to give a final concentration of 0.01 M, as was EDTA, to give a final concentration of 0.005 M, and SDS, to give a final concentration of 0.5%, as well as proteinase K, to give a final concentration of 20 mg/ml, after which the mixture was incubated at 56° C. for 20 min.

50 µl of the proteinase K-treated samples were taken up in 200 µl of 0.5 N NaOH in order to denature them. Eight 1:10 dilutions in 0.5 N NaOH were prepared from this mixture. In addition, a dilution series was prepared, in an analogous manner, from a known quantity of a plasmid possessing the DNA sequence to be detected, with this dilution series then acting as a standard. The dilution series were dotted onto a nylon membrane. The membrane was incubated at 80° C. in order to bind the DNA covalently and was then subjected to a Southern-hybridization using a labeled sample which was specific for adenovirus DNA (Chiorini, J. A. et al. (1995), loc sit.). A digoxygenin-labeled restriction fragment containing the adenovirus E1A gene was used as the sample. The adenovirus E1A DNA on the nylon membrane was visualized by the immunological detection of digoxygenin (Boehringer Mannheim GmbH, Mannheim). In the smallest dilution step for the E1A control plasmid, $2 \times 10^8$ single-stranded DNA molecules were loaded. In the case of the unfiltered control, the smallest dilution step at which material was detectable indicated an absolute quantity of about $5 \times 10^9$ adenovirus genomes. This would correspond to about $1 \times 10^{10}$ genomes/ml in the AAV preparation. In the case of the filtered aliquots, a weak signal can be detected in the smallest dilution step in most cases, which signal is weaker than that of the unfiltered control by about a factor of from $3 \times 10^3$ to $1 \times 10^4$ and would represent from $1 \times 10^7$ to $3 \times 10^7$ genomes/ml of the AAV preparation. However, the tests described in Example 2 showed that these genomes in the filtered aliquots are not associated with infectious particles but are present in non-infectious form. The filtration technique achieved a depletion of these adenovirus genomes by a factor of from $3 \times 10^3$ to $1 \times 10^4$.

Example 4
Detecting the Adenoviral Structural Protein IX in a Western Blot

The absence of the adenoviral structural protein IX in the filtrate was demonstrated in a Western blot using specific antibodies. 2 µl from filtered aliquots and from is unfiltered controls, as well as from adenovirus preparations, were in each case loaded, together with gel loading buffer, into one lane of a protein gel. The material was separated electrophoretically (Laemmli, U. K., Nature 227, 680–685, 1970) and electroblotted onto a nitrocellulose membrane. The Western blot was incubated with the rabbit antiserum which was specific for adenovirus structural protein IX. Specific bands were visualized using standard techniques. It was found that structural protein IX was removed by the filtration.

What is claimed is:

1. A process for separating mixed viruses of different sizes from each other, said process comprising filtering 1–10 ml of a virus-containing solution per 1 cm² of filtered surface resulting in a separation of more than 9 logs in virus titer of said viruses.

2. The process of claim 1, wherein the virus-containing solution is filtered through one or more filter membranes.

3. The process of claim 2, wherein the filter membrane is selected from the group of filter membranes consisting of polyvinylidene fluoride, polytetrafluoromethylene, polypropylene, modified or unmodified polyether sulfone, cellulose acetate, cellulose nitrate, polyamide, and regenerated cellulose.

4. The process of claim 3, wherein the filter membrane is cuprammonium-regenerated cellulose.

5. The process of claim 3, wherein the filter membrane is polyvinylidenefluoride.

6. The process of claim 2, wherein at least one of the filter membranes has a pore size of at most 120 nm.

7. The process of claim 6, wherein at least one of the filter membranes has a pore size of at most 60 nm.

8. The process of claim 7, wherein at least one of the filter membranes has a pore size of at most 50 nm.

9. The process of claim 8, wherein at least one of the filter membranes has a pore size of between 25–60 nm.

10. The process of claim 1, wherein the viruses are of a size of up to 120 nm.

11. The process of claim 10, wherein the viruses are of a size of up to 70 nm.

12. The process of claim 11, wherein the viruses are of a size of up to 60 nm.

13. The process of claim 1, wherein the difference in the sizes of the viruses to be separated is at least 5 nm.

14. The process of claim 13, wherein the difference in the sizes of the viruses to be seperated is at least 30 nm.

15. The process of claim 14, wherein the difference in the sizes of the viruses to be seperated is at least 40 nm.

16. The process of claim 1, wherein the viruses are of an essentially spherical shape.

17. The process of claim 16, wherein the viruses possess an icosahedral symmetry.

18. The process of claim 1, wherein the viruses are selected from a first group of viruses having a diameter of up to 60 nm and from either a second group of viruses having a diameter of from 60 nm up to 120 nm and/or a third group having a diameter of from 120 nm up to 250 nm.

19. The process of claim 18, wherein the viruses of the first group are selected from the group of viruses derived from Flaviviridae, papillomaviruses, papovaviruses, hepadnaviruses, picornaviruses, and parvoviruses.

20. The process of claim 19, wherein the viruses of the first group are derived from an adeno-associated virus.

21. The process of claim 18, wherein the viruses of the second group are selected from the group of viruses derived from influenza viruses, retroviruses, adenoviruses, reoviruses, and togaviruses.

22. The process of claim 21, wherein the viruses of the second group are derived from an adenovirus.

23. The process of claim 18, wherein the viruses of the third group are selected from the group of viruses derived from paramyxoviruses and herpesviruses.

24. The process of claim 23, wherein the viruses of the third group are derived from a herpesvirus.

25. The process of claim 1, wherein the virus-containing solution is prepurified.

26. The process of claim 25, wherein said prepurification is effected by means of one or more density gradients or one or more prefiltrations.

27. The process of claim 26, wherein one or more membrane filters are used in said prefiltration.

28. The process of claim 27, wherein the membrane filter for prepurifying said viruses of the first group has a pore size of at least 60 nm, while the membrane filter for prepurifying viruses of the first or second group has a pore size of at least 120 nm, and the membrane filter for prepurifying viruses of the first, second, or third group has a pore size of at least 250 nm.

29. The process of claim 1, wherein the pH of the virus-containing solution is 6–10.

30. The process of claim 29, wherein the pH of the virus-containing solution is 7.0–8.5.

31. The process of claim 30, wherein the pH of the virus-containing solution is 8.0.

32. The process of claim 1, wherein the virus-containing solution further comprises protein.

33. The process of claim 32, wherein said protein is in the form of fetal calf serum or serum albumin.

34. The process of claim 32, wherein the proportion of protein in the virus-containing solution is not more than 30% (v/v).

35. The process of claim 34, wherein the proportion of protein in the virus-containing solution is not more than 15% (v/v).

36. The process of claim 35, wherein the proportion of protein in the virus-containing solution is not more than 10% (v/v).

37. The process of claim 1, wherein 2–5 ml of solution are filtered per 1 $cm^2$ of filter surface.

38. The process of claim 37, wherein not more than 2–2.5 ml of solution are filtered per 1 $cm^2$ of filter surface.

* * * * *

UNITED STATES PATENT AND TRADEMARK OFFICE
CERTIFICATE OF CORRECTION

PATENT NO. : 6,479,273 B1
DATED : November 12, 2002
INVENTOR(S) : Bogedain et al.

It is certified that error appears in the above-identified patent and that said Letters Patent is hereby corrected as shown below:

Column 8,
Line 9, "pref ilter" should be -- prefilter --.

Column 9,
Line 31, "semiguantitative" should be -- semiquantitative --.

Column 10
Line 67, "seperated" should be -- separated --.

Column 11,
Line 2, "seperated" should be -- separated --.

Signed and Sealed this

Twenty-eighth Day of June, 2005

JON W. DUDAS
*Director of the United States Patent and Trademark Office*